United States Patent [19]

Schulz et al.

[11] 4,052,448
[45] Oct. 4, 1977

[54] ORGANIC ACIDS AND PROCESS FOR PREPARING SAME

[75] Inventors: J. Gustav Schulz, Pittsburgh; Edward T. Sabourin, Allison Park, both of Pa.

[73] Assignee: Gulf Research & Development Company, Pittsburgh, Pa.

[21] Appl. No.: 696,752

[22] Filed: June 16, 1976

[51] Int. Cl.² ........................ C07C 63/33; C08J 9/14
[52] U.S. Cl. ....................... 260/515 H; 260/515 M; 260/515 P; 260/2.5 R; 260/2.5 HA
[58] Field of Search ........... 260/515 P, 515 H, 515 M

[56] References Cited

U.S. PATENT DOCUMENTS

| | | | |
|---|---|---|---|
| 2,726,262 | 12/1955 | Grosskinsky et al. | 260/515 P |
| 3,153,666 | 10/1964 | Higuchi et al. | 260/515 H |

Primary Examiner—James O. Thomas, Jr.
Assistant Examiner—G. T. Breitenstein

[57] ABSTRACT

A mixture of polycyclic aromatic polycarboxylic acids carrying nuclear nitro groups that is substantially soluble in acetone but substantially insoluble in water and a process for preparing the mixture.

7 Claims, 1 Drawing Figure

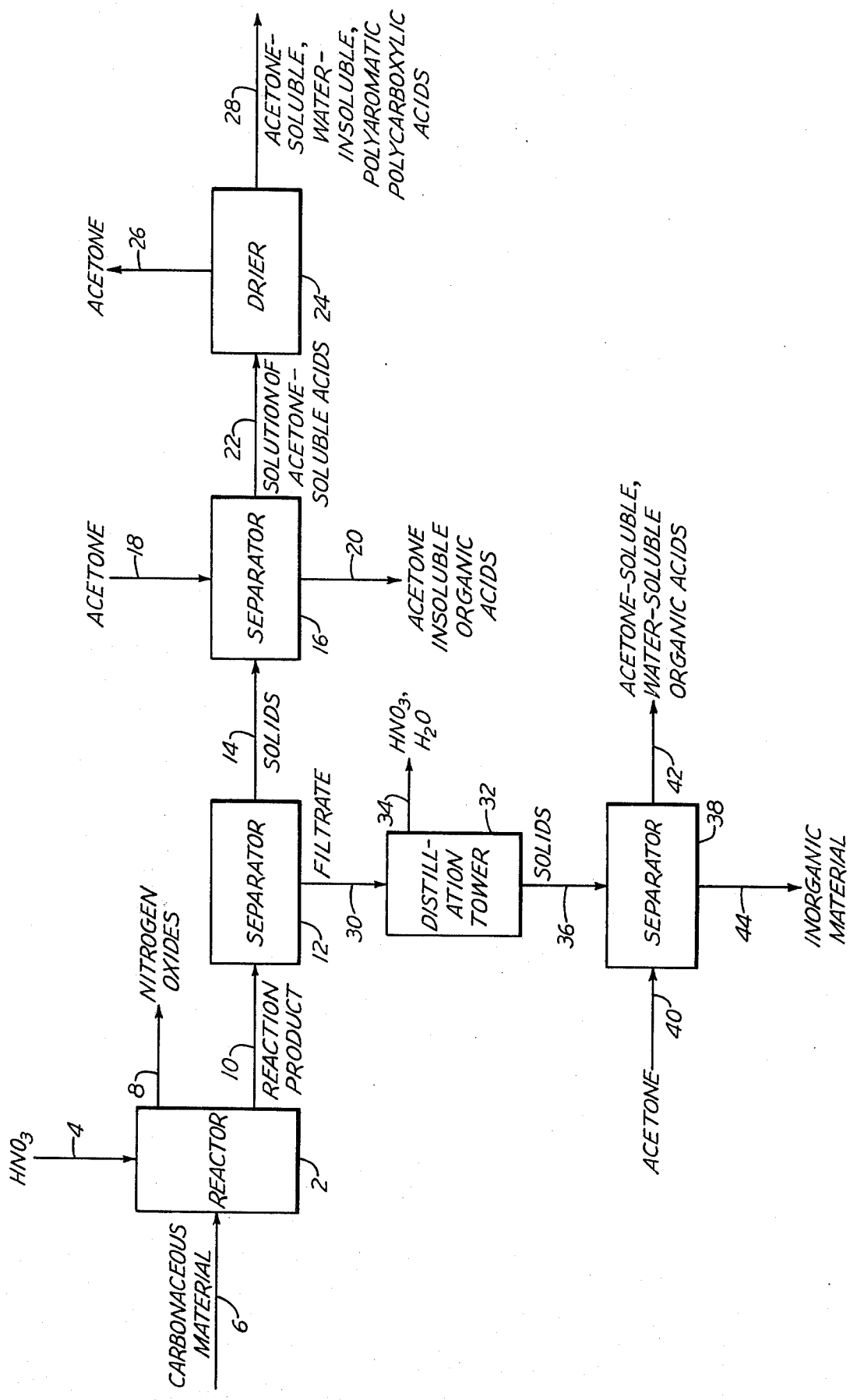

ORGANIC ACIDS AND PROCESS FOR PREPARING SAME

BACKGROUND OF THE INVENTION

1. Field of the Invention

This invention relates to a mixture of polycyclic aromatic polycarboxylic acids carrying nuclear nitro groups that is substantially soluble in acetone but substantially insoluble in water and a process for preparing the mixture by treating a carbonaceous material with nitric acid.

2. Description of Prior Art

Treating a carbonaceous material, such as coal, with nitric acid to obtain carboxylic acids is shown in U.S. Pat. Nos. 2,555,410 to Howard, 2,726,262 to Grosskinsky et al, 2,949,350 to Heinze et al, 2,991,189 to Rickert and 3,173,947 to Benning et al. In each of these the acids obtained are said to be water soluble. Creigton et al in U.S. Pat. No. 3,468,943 are interested in passing coal through a screw conveyor and at spaced apart intervals feeding appropriate quantities of concentrated nitric acid so that it is completely reacted with the coal before the coal arrives at the next nitric acid feed point to obtain humic acids which are said to be partially soluble in sodium hydroxide solution but substantially insoluble in water.

SUMMARY OF THE INVENTION

We have prepared novel mixtures of polycyclic aromatic polycarboxylic acids carrying nuclear nitro groups that are substantially soluble in acetone but substantially insoluble in water. The individual components of said mixtures are believed to be composed of condensed and/or non-condensed benzene rings, with an average number of benzene rings in the individual molecules ranging from two to about 10, but generally from three to about eight. On the average, the number of carboxyl groups carried by the individual molecules will range from about four to about 10, generally from about six to about eight, and the average number of nitro groups from about one to about four, generally from about two to about three. The average molecular weight of the mixture will range from about 600 to about 1500, generally from about 700 to about 1000, and the average neutral equivalent will range from about 80 to about 200, generally from about 100 to about 150. A typical analysis of the novel mixture is defined below in Table I in approximate amounts.

TABLE I

| | Weight Per Cent | |
|---|---|---|
| | Broad Range | Preferred Range |
| Carbon | 50 to 60 | 52 to 56 |
| Hydrogen | 3 to 5 | 3.7 to 4.4 |
| Nitrogen | 3 to 6 | 4 to 5 |
| Oxygen | 25 to 45 | 30 to 40 |
| Sulfur | 0.2 to 0.5 | 0.3 to 0.5 |
| Ash | 0.1 to 5 | 0.3 to 3 |

A preferred and novel procedure for obtaining the above novel mixtures is described in reference to FIG. I. There is introduced into reactor 2 by line 4 an aqueous solution of nitric acid and by line 6 a carbonaceous material. The nitric acid can have a concentration of about 5 to about 90 percent, but preferably will be in the range of about 10 to about 70 percent. The carbonaceous material is preferably a solid in the form of a slurry, for example, an aqueous slurring containing the carbonaceous material in particulate form and from about 50 to about 90 weight percent of water.

The solid carbonaceous material that can be used herein can have the following composition on a moisture-free basis:

TABLE II

| | Weight Per Cent | |
|---|---|---|
| | Broad Range | Preferred Range |
| Carbon | 45–95 | 60–92 |
| Hydrogen | 2.5–7 | 4–6 |
| Oxygen | 2.0–45 | 3–25 |
| Nitrogen | 0.75–2.5 | 0.75–2.5 |
| Sulfur | 0.3–10 | 0.5–6 |

The carbon and hydrogen content of the carbonaceous material will reside primarily in multi-ring aromatic compounds (condensed and/or uncondensed), heterocyclic compounds, etc. Oxygen and nitrogen are believed to be present primarily in chemical combination. Some of the sulfur is believed to be present in chemical combination with the aromatic compounds and some in chemical combination with inorganic elements associated therewith, for example, iron and calcium.

In addition to the above the solid carbonaceous material being treated herein will also contain solid, primarily inorganic, compounds which will not be converted to the desired organic mixture claimed herein, which are termed ash, and are composed chiefly of compounds of silicon, aluminum, iron and calcium, with smaller amounts of compounds of magnesium, titanium, sodium and potassium. The ash content of the carbonaceous material treated herein will amount to less than about 50 weight percent, based on the moisture-free carbonaceous material, but, in general, will amount to about 0.1 to about 30 weight percent, usually about 0.5 to about 20 weight percent.

Anthracitic, bituminous and subbituminous coal, lignitic materials, and other type of coal products referred to in ASTM D-388 are exemplary of the solid carbonaceous materials which can be treated in accordance with the process defined herein to produce the claimed organic mixture. Some of these carbonaceous materials in their raw state will contain relatively large amounts of water. These can be dried prior to use herein. The carbonaceous material, prior to use, is preferably ground in a suitable attrition machine, such as a hammermill, to a size such that at least about 50 percent of the carbonaceous material will pass through a 40-mesh (U.S. Series) sieve. As noted, the carbonaceous material is slurried in a suitable carrier, preferably water, prior to reaction with nitric acid. If desired, the carbonaceous material can be treated, prior to reaction herein, using any conventional means, to remove therefrom any materials forming a part thereof that will not be converted in reaction with nitric acid herein.

The reactant mixture in reactor 2 is stirred while being maintained at a temperature of about 15° to about 200° C., preferably about 50° to about 100° C., and a pressure of about atmospheric to about 1000 pounds per square inch gauge (about atmospheric to about 70 kilograms per square centimeter), preferably about atmospheric to about 500 pounds per square inch gauge (about atmospheric to about 35 kilograms per square centimeter) for about 0.5 to about 15 hours, preferably about two to about 6 hours. In order to obtain the desired mixture herein without losing appreciable amounts of carboxyl and/or nitro groups on the acids that are formed during the oxidation, and to obtain the desired acids in high yields in reactor 2, it is absolutely critical that the reaction conditions therein, namely nitric acid concentration, temperature, pressure and reaction time, be so correlated to minimize and, preferably, to avoid decarboxylation and denitrofication. Gaseous products, such as nitrogen oxides, can be removed from reaction 2 by line 8.

The reaction product is removed from reactor 2 by line 10. We have found that the reaction product is soluble in, or reactable with, sodium hydroxide. At this point it is necessary to separate the oxidized product from the water and nitric acid associated therewith. This separation must be accomplished in a manner so that the carboxyl and nitro groups are not removed from the acid product. Distillation for the removal of water will not suffice, because under the conditions required for such separation, a significant loss of carboxyl groups and nitro groups would occur. Accordingly, we have found that a mechanical separation will suffice. The reaction product in line 10 is therefore led to a separator 12, which can be, for example, a filter or a centrifuge.

The solids that are recovered in separator 12, also soluble in sodium hydroxide, are led by line 14 to a separator 16 wherein they are subjected to extraction with acetone that is introduced therein by line 18. Such separation can be carried out at a temperature of about 20° to about 60° C., preferably about 25° to about 50° C., and a pressure of about atmospheric to about 500 pounds per square inch gauge (about atmospheric to about 35 kilograms per square centimeter), preferably about atmospheric to about 100 pounds per square inch gauge (about atmospheric to about 7 kilograms per square centimeter). The solid material, insoluble in acetone, is removed from separator 16 by line 20 and the acetone solution of the novel acid mixture by line 22. The acetone solution is then led to drier 24 wherein acetone is separated therefrom by line 26 and the desired novel acetone-soluble, water-insoluble polyaromatic, polycarboxylic acid mixture claimed herein is recovered in line 28. As before, the acid mixture in drier 24 must be treated by so correlating the conditions therein to remove acetone therefrom in such manner so as to minimize and, preferably, avoid, decarboxylation and denitrofication. The temperature can be in the range of about 10° to about 60° C., preferably about 20° to about 50° C., the presssure about 10 millimeters of mercury to about atmospheric, preferably about 30 millimeters of mercury to about atmospheric, for about 0.5 to about 24 hours, preferably about 1 to about 5 hours.

The filtrate obtained in separator 12 is removed therefrom by line 30. In all cases the filtrate will contain water, nitric acid and most of the inorganic material (ash) that was present in the carbonaceous charge. In addition there can also be present other oxidized material, which are primarily acetone-soluble, water-soluble organic acids.

Separation of the filtrate into its component parts can be effected as follows. It can be passed to distillation tower 32 maintained at a temperature of about 50° to about 100° C., preferably about 70° to about 90° C. and a pressure of about 10 millimeters of mercury to about atmospheric, preferably about 30 millimeters of mercury to about atmospheric. Under these conditions nitric acid and water are removed from distillation tower 32 by line 34 and solids by line 36. The solids are led to separator 38 where they are subjected to extraction with acetone introduced therein by line 40. The conditions in separator 38 are similar to those used in separator 16. A mixture of acetone-soluble, water-soluble organic acids is removed from separator 38 by line 42 and substantially all of the inorganic material that was present in the carbonaceous charge by line 44.

DESCRIPTION OF PREFERRED EMBODIMENTS

Several runs were carried out in which a North Dakota Lignite analyzing as follows, on a substantially moisture-free basis, was subjected to oxidation using nitric acid as the oxidant: 65.03 weight percent carbon, 4.0 weight percent hydrogen, 27.0 weight percent oxygen, 0.92 weight percent sulfur, 0.42 weight percent nitrogen and 0.04 weight percent moisture. The ash was further analyzed and found to contain 43 weight percent oxygen, 7.8 weight percent sulfur and the remainder metals. In each of Runs Nos. 3 to 8, the data of which are summarized below in Table III, 70 percent aqueous nitric acid was used. In Runs Nos. 1 and 2, the aqueous nitric acid used had a concentration of 90 percent. In Runs Nos. 4 to 8, over a period of 2 hours, 100 milliliters of the defined nitric acid was gradually added to the stirred slurry containing 100 grams of powdered lignite defined above (corresponding to 67.5 grams of moisture-free feed) and 370 grams of water while maintaining the contents at selected temperature levels and atmospheric pressure. In Run No. 3, otherwise identical to Runs Nos. 4 to 8, a five-hour reaction time was employed. In the remaining runs solid lignite was added gradually to 411 milliliters of nitric acid at a rate sufficient to maintain the reaction temperature. Nitrogen oxides were permitted to escape from the reaction zone as they evolved.

At the end of the reaction period the product slurry was withdrawn from the reaction zone and filtered to obtain a solids fraction and a filtrate. The solids were extracted with acetone at atmospheric temperature and pressure. The acetone solution was then subjected to evaporation at atmospheric temperature and pressure to obtain the novel mixture herein. The acetone insoluble portion was found to be soluble in sodium hydroxide and to comprise organic acids of a relatively higher molecular weight than the acetone-soluble portion.

The filtrate in Runs Nos. 7 and 8 was found to consist essentially of unreacted nitric acid, water and inorganic materials (ash). However, in each of Runs Nos. 1 to 6 some acetone soluble, water-soluble organic acids were also found. The work-up of the filtrate was carried out as follows. Iniatially the filtrate was subjected to distillation to separate unreacted nitric acid and water therefrom. The remaining solids were subjected to extraction with acetone at atmospheric temperature and atmospheric pressure. The acetone solution was dried to remove acetone therefrom, resulting in the recovery of small amounts of the acetone-soluble, water-soluble organic acids substantially completely soluble in sodium hydroxide. The average molecular weight of the mixtures obtained was about 800 and the average neutral equivalent about 110. The residue was mainly ash. The data obtained are summarized below in Table III.

TABLE III

| Run No. | Temperature, °C | Reaction Time, Hours | Acetone-Soluble Water-Insoluble Product, Grams | Analysis of Product, Weight Per Cent | | | | | |
|---|---|---|---|---|---|---|---|---|---|
| | | | | Carbon | Hydrogen | Nitrogen | Oxygen | Sulfur | Ash |
| 1 | 15 | 2 | 85.6 | 48.03 | 3.33 | 4.53 | 41.06 | 0.24 | 2.81 |
| 2 | 30 | 2 | 71.4 | 48.03 | 3.57 | 5.10 | 40.63 | 0.19 | 2.48 |
| 3 | 50 | 5 | 67.0 | 56.30 | 4.80 | 4.60 | 33.27 | 0.31 | 0.72 |
| 4 | 70 | 2 | 51.1 | 55.52 | 3.72 | 4.70 | 35.13 | 0.30 | 0.63 |
| 5 | 90 | 2 | 52.5 | 53.94 | 4.38 | 4.61 | 36.39 | 0.25 | 0.43 |
| 6 | 110 | 2 | 35.5 | 54.53 | 4.36 | 4.51 | 35.35 | 0.27 | 0.98 |
| 7 | 130 | 2 | 7.1 | 56.8 | 4.20 | 4.31 | 33.59 | 0.24 | 0.86 |
| 8 | 150 | 2 | 4.7 | 61.65 | 5.06 | 4.03 | 27.95 | 0.26 | 1.05 |

Note from the above table that while an acetone-soluble, water-insoluble material was obtained in each of the runs, the largest amount was obtained at the lower temperatures.

Although we have stated above that the novel composition is acetone-soluble and we have shown the use of acetone as suitable in the process defined herein, this has been done merely as a characterization of the composition and to exemplify one embodiment of our process. Many polar solvents can be used in place of acetone herein. Among the polar solvents that have been used are methanol, ethanol, isopropanol, methyl ethyl ketone, tetrahydrofuran, dioxane, cyclohexanone, etc. The use of such solvents, therefore, falls within the scope of the invention claimed herein.

Since the novel mixture herein has abundant functionality in both carboxyl and nitro groups, it is apparent that the mixture lends itself to many known chemical reactions, for example, esterification of the carboxyl groups, hydrogenation of the nitro groups to amines, etc. We have found that the novel mixtures defined herein are effective blowing agents for the purpose of incorporating the same in well-known resins, such as polyethylene, to permanently increase the volume of the resin. This is shown in our copending Application Ser. No. 696,743, filed concurrently herewith.

Obviously, many modifications and variations of the invention, as hereinabove set forth, can be made without departing from the spirit and scope thereof and, therefore, only such limitations should be imposed as are indicated in the appended claims.

We claim:

1. A process for preparing a mixture of polycyclic aromatic polycarboxylic acids carrying nuclear nitro groups that is soluble in acetone but insoluble in water which comprises subjecting a slurry containing coal to reaction with aqueous nitric acid having a concentration of about 5 to about 90 percent at a temperature of about 15° to about 200° C. for about 0.5 to about 15 hours, mechanically separating the solids in the resulting slurry, extracting the resulting solids with a polar solvent and then separating the polar solvent from the extract to recover the desired carboxylic acid mixture.

2. The process of claim 1 wherein said polar solvent is acetone.

3. The process of claim 1 wherein the nitric acid has a concentration of about 10 to about 70 percent and the reaction is carried out at a temperature of about 50° to about 100° C. for about two to about six hours (preferred range).

4. The process of claim 1 wherein the mechanical separation is effected by filtration.

5. The process of claim 1 wherein the acetone separation is effected by subjecting the acetone extract to drying.

6. The process of claim 1 wherein the coal is lignite.

7. A mixture of polycyclic aromatic polycarboxylic acids carrying nuclear nitro groups that is soluble in acetone but insoluble in water resulting from the process of claim 1.

* * * * *